US009095316B2

(12) United States Patent
Welch et al.

(10) Patent No.: US 9,095,316 B2
(45) Date of Patent: Aug. 4, 2015

(54) SYSTEM FOR GENERATING ALARMS BASED ON ALARM PATTERNS

(75) Inventors: James P. Welch, Mission Viejo, CA (US); Brian Spencer Long, Aliso Viejo, CA (US)

(73) Assignee: Masimo Corporation, Irvine, CA (US)

( * ) Notice: Subject to any disclaimer, the term of this patent is extended or adjusted under 35 U.S.C. 154(b) by 490 days.

(21) Appl. No.: 13/450,942

(22) Filed: Apr. 19, 2012

(65) Prior Publication Data

US 2012/0286955 A1 Nov. 15, 2012

Related U.S. Application Data

(60) Provisional application No. 61/477,513, filed on Apr. 20, 2011.

(51) Int. Cl.
G08B 23/00 (2006.01)
A61B 5/00 (2006.01)
A61B 5/0205 (2006.01)
A61B 5/1455 (2006.01)
G08B 21/04 (2006.01)
A61B 5/0245 (2006.01)

(52) U.S. Cl.
CPC ............ *A61B 5/746* (2013.01); *A61B 5/0205* (2013.01); *A61B 5/14551* (2013.01); *A61B 5/02455* (2013.01); *G08B 21/0453* (2013.01)

(58) Field of Classification Search
CPC ........ A61B 5/00; A61B 5/0002; G06F 19/00; G08B 21/00; G08B 21/22; G08B 25/016; G08B 21/0288; G08B 21/0446
USPC ...................................................... 340/573.1
See application file for complete search history.

(56) References Cited

U.S. PATENT DOCUMENTS

| 4,960,128 | A | 10/1990 | Gordon et al. |
|---|---|---|---|
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |

(Continued)

OTHER PUBLICATIONS

Eldor et al., "A device for monitoring ventilation during anaesthesia; the paratracheal audible respiratory monitor", Canadian Journal of Anaesthesia, 1990, vol. 9, No. 1, p. 95-98.

*Primary Examiner* — Jennifer Mehmood
*Assistant Examiner* — Rufus Point
(74) *Attorney, Agent, or Firm* — Knobbe Martens Olson & Bear LLP

(57) ABSTRACT

An alarm system can include one or more processors. Such processors can receive physiological parameter data associated with a patient. The one or more processors can also select an alarm pattern based at least in part on an indicator of an attribute of the patient. The alarm pattern can include a plurality of different thresholds and corresponding periods of time. Further, the one or more processors can generate an alarm when a value associated with the physiological parameter data satisfies at least one threshold of the plurality of thresholds for the period of time corresponding to the at least one threshold.

20 Claims, 8 Drawing Sheets

(56) References Cited

U.S. PATENT DOCUMENTS

| | | |
|---|---|---|
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,865,736 A | 2/1999 | Baker, Jr. et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada et al. |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kianl et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |

(56) References Cited

U.S. PATENT DOCUMENTS

| | | |
|---|---|---|
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,123,950 B2 | 10/2006 | Mannheimer |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,629,889 B2 * | 12/2009 | Sachanandani et al. ... 340/573.1 |
| 7,639,145 B2 * | 12/2009 | Lawson et al. ............. 340/573.1 |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,031,076 B2 * | 10/2011 | Sachanandani et al. ... 340/573.1 |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,223,023 B2 * | 7/2012 | Sachanandani et al. ... 340/573.1 |
| 8,456,309 B2 * | 6/2013 | Sachanandani et al. ... 340/573.1 |
| 2003/0158466 A1 * | 8/2003 | Lynn et al. .................... 600/300 |

(56) References Cited

U.S. PATENT DOCUMENTS

| | | | |
|---|---|---|---|
| 2006/0030890 A1* | 2/2006 | Cosentino et al. | 607/5 |
| 2006/0074338 A1* | 4/2006 | Greenwald et al. | 600/549 |
| 2006/0149144 A1* | 7/2006 | Lynn et al. | 600/323 |
| 2008/0157980 A1* | 7/2008 | Sachanandani et al. | 340/573.1 |
| 2009/0209839 A1* | 8/2009 | Ochs et al. | 600/364 |
| 2009/0275808 A1* | 11/2009 | DiMaio et al. | 600/301 |

* cited by examiner

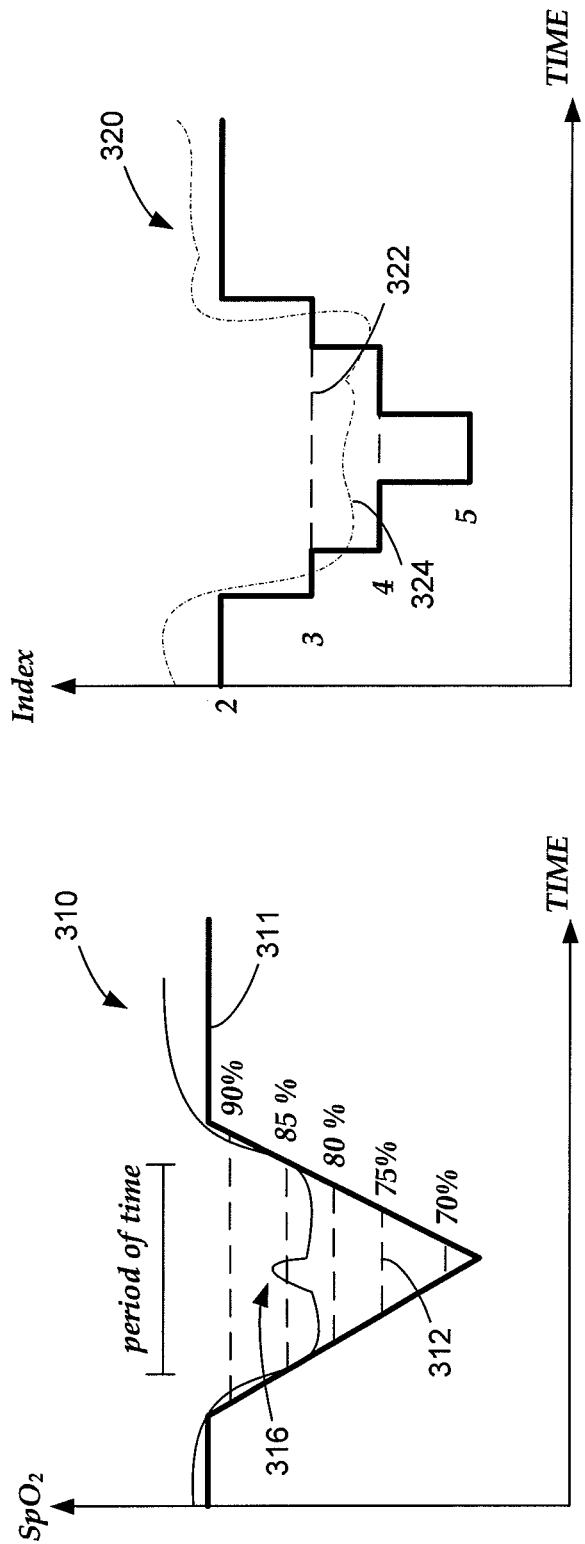

SYSTEM FOR GENERATING ALARMS BASED ON ALARM PATTERNS

CROSS REFERENCE TO RELATED APPLICATION

This application is a non-provisional of U.S. Provisional Patent Application No. 61/477,513, filed Apr. 20, 2011, titled "SYSTEMS FOR GENERATING ALARMS BASED ON ALARM PATTERNS," which is hereby incorporated by reference in its entirety herein.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a patient's physiological parameters. Physiological parameters include, for example, blood pressure, respiratory rate, oxygen saturation ($SpO_2$) level, other blood constitutions and combinations of constituents, and pulse, among others. Clinicians, including doctors, nurses, and certain other caregiver personnel use the physiological parameters obtained from the patient to diagnose illnesses and to prescribe treatments. Clinicians can also use the physiological parameters to monitor a patient during various clinical situations to determine whether to increase the level of care given to the patient. Various patient monitoring devices are commercially available from Masimo Corporation ("Masimo") of Irvine, Calif.

During and after surgery and in other care situations, one or more physiological parameters of a patient can be monitored. An alarm can be generated based on such monitoring to alert a clinician (such as a nurse, doctor, or the like) of a potentially clinically significant patient condition.

SUMMARY OF THE DISCLOSURE

In certain embodiments, a method can reduce nuisance alarms. Physiological information associated with a patient can be received. A physiological parameter associated with the patient can be calculated based at least in part on the received physiological information. Under control of one or more processors, an alarm pattern can be selected based at least in part on a characteristic of the patient. The alarm pattern can include a plurality of thresholds each having corresponding periods of time. Whether to generate an alarm can be determined based at least in part on a comparison over time of the physiological parameter to a value computed using the alarm pattern.

In various embodiments, another method can reduce nuisance alarms. A physiological parameter associated with a patient can be received. Under control of one or more processors, an alarm pattern can be selected. The alarm pattern can include a plurality of thresholds each having corresponding periods of time. Whether to generate an alarm can be determined based at least in part on a comparison over time of the physiological parameter to a value computed using the alarm pattern.

In some embodiments, an alarm system can include one or more processors. Such processors can receive physiological parameter data associated with a patient. The one or more processors can also select an alarm pattern based at least in part on an indicator of an attribute of the patient. The alarm pattern can include a plurality of different thresholds and corresponding periods of time. Further, the one or more processors can generate an alarm when a value associated with the physiological parameter data satisfies at least one threshold of the plurality of thresholds for the period of time corresponding to the at least one threshold.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIG. 3A illustrates an embodiment of an alarm pattern for $SpO_2$.

FIG. 3B illustrates an embodiment of an alarm pattern for an index.

DETAILED DESCRIPTION

Figure 1:
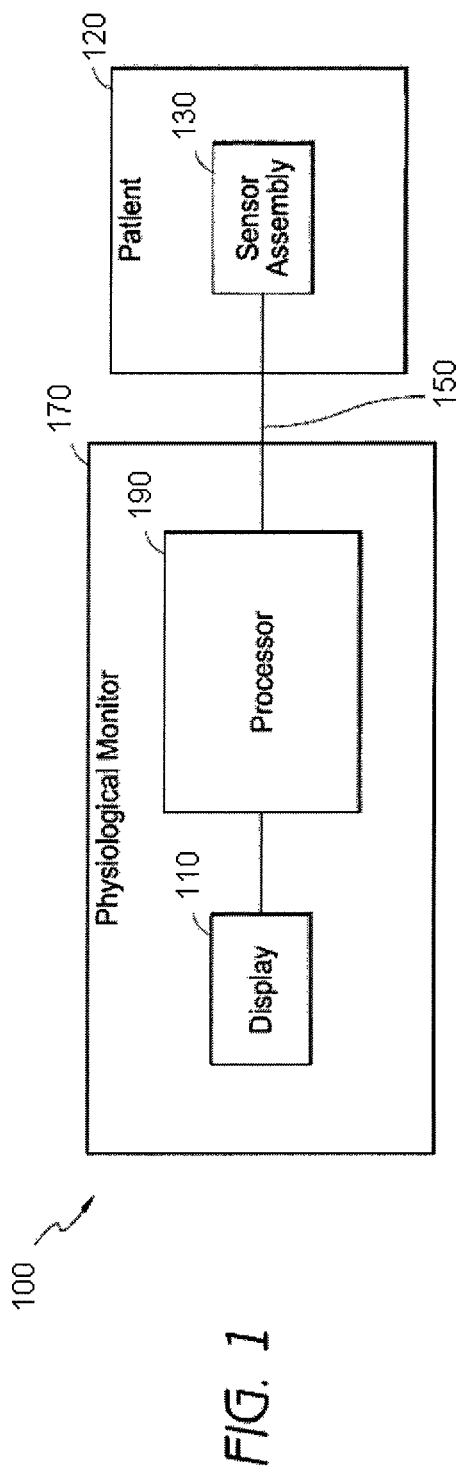
FIG. 1 is a block diagram illustrating a physiological monitoring system in accordance with embodiments of the disclosure.

Patient monitoring systems can be used to monitor one or more physiological parameters of a patient, such as oxygen saturation ($SpO_2$), pulse rate, respiratory rate, heart rate, or the like. The one or more physiological parameters can be determined, for example, from data obtained from one or more sensors (e.g., acoustic and/or optical sensors) and/or other instruments. When the one or more physiological parameters go outside of a predetermined range, an alarm can be generated to alert a clinician of a patient condition. The alarm can include, for example, an audio and/or visual indicator.

Alarms can be generated by patient monitoring systems that compare a physiological parameter to a threshold. A significant number of alarms generated by such patient monitoring systems may not correspond to clinically significant patient conditions. An alarm that does not correspond to a clinically significant patient condition may be referred to as a nuisance alarm. Clinicians can tend to ignore alarms when nuisance alarms are frequently generated, which may lead to ignoring an alarm related to a clinically significant event. At the same time, hospitals and clinicians can be reluctant to adjust a parameter threshold value for generating an alarm because they do not want to miss a clinically significant event.

There are disadvantages associated with some existing methods of reducing nuisance alarms. For example, some methods of reducing nuisance alarms are computationally complex. Not only may this require more complex hardware and additional power consumption, but this may also make it difficult to teach clinicians about the alarms being generated. As a result, clinicians may have a less intuitive understanding of the alarms and what they indicate. Alternatively or additionally, some methods of reducing nuisance alarms have encountered difficulty detecting certain patient conditions. This has been due to the methods of generating the alarms in some systems. Further, some methods treat all patients the same. Accordingly, more nuisance alarms may be generated because detecting patient conditions may not be tailored to the patient. One or more of these problems, among others, can be overcome based on the principles and advantages described herein.

This disclosure describes, among other features, systems and methods for using alarm patterns to improve alarm generation such that more alarms correspond to clinically significant patient conditions and fewer alarms are nuisance alarms. An alarm system can receive and/or calculate physiological parameter data associated with a patient. Based on a characteristic of the patient, an alarm pattern can be selected. The alarm pattern can include a plurality of different thresholds and corresponding periods of time. An alarm can then be generated based on comparing a value associated with the physiological parameter data with at least one of the plurality of thresholds over time. For example, an alarm can be generated when the value associated with the physiological parameter data satisfies a threshold of the plurality of thresholds for the period of time corresponding to the threshold. As another example, an alarm can be generated when the value associated with the physiological parameter is within a range for a predetermined period of time.

With reference to FIG. 1, an embodiment of a physiological monitoring system 100 is shown. The physiological monitoring system 100 can also be referred to as a patient monitoring system. In the physiological monitoring system 100, a medical patient 120 is monitored using one or more sensor assemblies 130, each of which transmits a signal over a cable 150 or other communication link or medium to a physiological monitor 170. The physiological monitor 170 includes a processor 190 and, optionally, a display 110. The one or more sensor assemblies 130 include sensing elements such as, for example, acoustic piezoelectric devices, electrical ECG leads, optical sensors, or the like. The sensor assemblies 130 can generate respective signals by measuring a physiological parameter of the patient 120. The signals are then processed by one or more processors 190. The one or more processors 190 then communicate the processed signal to the display 110. In an embodiment, the display 110 is incorporated in the physiological monitor 170. In another embodiment, the display 110 is separate from the physiological monitor 170. In one embodiment, the monitoring system 100 is a portable monitoring system. In another embodiment, the monitoring system 100 is a pod, without a display, that is adapted to provide physiological parameter data to a display or to another device (such as a storage device) over a network.

For clarity, a single block is used to illustrate the one or more sensors 130 shown in FIG. 1. It should be understood that the sensor assembly 130 shown is intended to represent one or more sensors. In an embodiment, the one or more sensor assemblies 130 include a single sensor of one of the types described below. In another embodiment, the one or more sensor assemblies 130 include one or more optical sensors. In still another embodiment, the one or more sensor assemblies 130 one or more ECG sensors, acoustic sensors, bioimpedance sensors, capnography sensors, and the like. In each of the foregoing embodiments, additional sensors of different types are also optionally included. Other combinations of numbers and types of sensors are also suitable for use with the physiological monitoring system 100.

In some embodiments of the system shown in FIG. 1, the hardware used to receive and process signals from the sensors are housed within the same housing. In other embodiments, some of the hardware used to receive and process signals is housed within a separate housing. In addition, the physiological monitor 170 of certain embodiments includes hardware, software, or both hardware and software, whether in one housing or multiple housings, used to receive and process the signals transmitted by the sensors 130.

Figure 2:
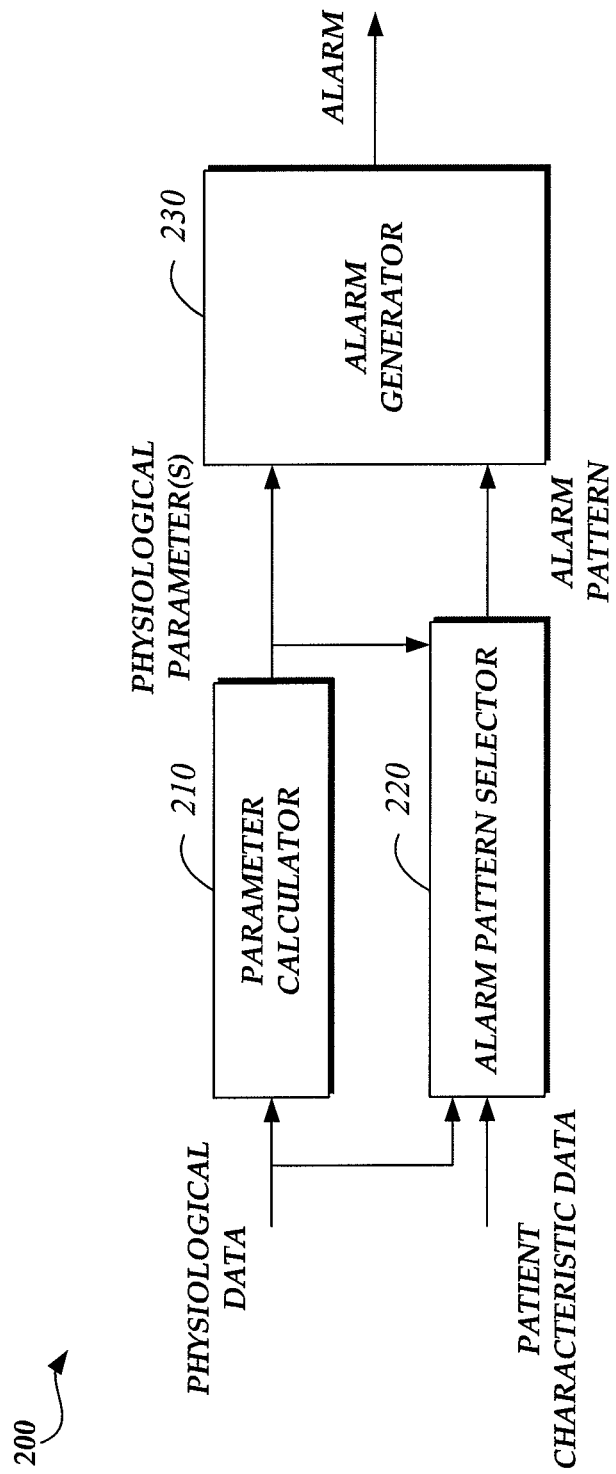
FIG. 2 illustrates a block diagram of an embodiment of a physiological monitoring system for generating an alarm based on an alarm pattern.

Referring to FIG. 2, a block diagram illustrating an embodiment of a physiological monitoring system 200 for generating an alarm will be described. The physiological monitoring system 200 can be used to process physiological data obtained from one or more sensors, which can include, for example, the sensor assembly 130 (FIG. 1) or any of the sensors described herein. Such processing can include calculating one or more physiological parameters and/or an index of two or more physiological parameters. The physiological monitor system 200 can also be used to process patient characteristic data. Based on the patient characteristic data and/or physiological data, an alarm pattern can be selected. Then an alarm can be generated based on comparing a physiological parameter to an alarm pattern. The physiological monitoring system 200 can be included as part of the physiological monitor 170 (FIG. 1), in some embodiments.

The physiological monitoring system 200 can include a physiological parameter calculator 210, an alarm pattern selector 220, and an alarm generator 230. The physiological parameter calculator 210, the alarm pattern selector 220, and the alarm generator 230 can each be implemented using one or more processors. In some embodiments, the physiological parameter calculator 210, the alarm pattern selector 220, and the alarm generator 230 can be implemented in the same processor. In other embodiments, two or more processors can implement the physiological parameter calculator 210, the alarm pattern selector 220, and the alarm generator 230.

One or more physiological parameters can be computed by the parameter calculator 210. The parameter calculator 210 can be included, for example, as part of the processor 190 (FIG. 1). Physiological data can be provided to the parameter calculator 210, for example, via any of the sensors described herein. The parameter calculator 210 can calculate one or more physiological parameters based on the physiological data and provide one or more physiological parameters to the alarm generator 230. In some embodiments, the parameter calculator can also provide one or more physiological parameters to the alarm pattern selector 220. Example physiological parameters can include, but are not limited to, $SpO_2$, respiratory rate, pulse rate, blood pressure, temperature, $EtCO_2$, bioimpedance values, and the like. Physiological parameters can be calculated using any suitable parameter calculation technique.

Alternatively or additionally, the parameter calculator 210 can calculate an index based on two or more physiological parameters. The calculated index may be a numerical value that represents some combination of individual parameter values. Each parameter can be normalized to a numerical value. The numerical value can correspond to a variation in a parameter value from a typical parameter value. The index can be computed by adding, or otherwise combining, numerical values for two or more parameters. For example, an index can be created using a modified early warning score (MEWS), and the index can be compared to a plurality of thresholds in an alarm pattern (see, e.g., FIG. 3B). The index could also be a Leeds Teaching Hospitals score or some other index based on a different scoring system.

In an illustrative example, an index can be computed based on heart rate, $SpO_2$, and respiratory rate. A typical value for heart rate, $SpO_2$, and respiratory rate can be assigned a score of zero. The score of each of these parameters can be incremented for parameter values that indicate that it is more likely that the patient is experiencing a clinically significant event. For instance, a typical heart rate of 90 beats per minute can be assigned to a score of zero, a heart rate of 80 or 100 beats per minute (BPM) can be assigned to a score of one, and a heart rate of 70 or 120 BPM can be assigned to a score of two. Example scores and corresponding parameter values for heart rate, percent $SpO_2$, and respiratory rate in breaths per minute (bpm) are provided in Table 1. These scores and corresponding values are chosen for example purposes only and can vary considerably in other embodiments.

Based on the example data in Table 1, when a patient's heart rate is 120 BPM, $SpO_2$ is 90%, and respiratory rate is 26 bpm, the index can be 6 (2+1+3=6), for example. In some implementations, the index can be computed in real time. An alarm can be generated when the index satisfies a predetermined threshold, for example, based on any combination of features described herein.

TABLE 1

| Parameter | Score | | | | | | |
|---|---|---|---|---|---|---|---|
| | 3 | 2 | 1 | 0 | 1 | 2 | 3 |
| Heart Rate (BPM) | 60 | 70 | 80 | 90 | 100 | 120 | 140 |
| % $SpO_2$ | 80 | 85 | 90 | 95 | 90 | 85 | 80 |
| Respiratory Rate (breaths per min) | 26 | 24 | 21 | 18 | 10 | 6 | 4 |

In some embodiments, the parameter calculator 210 can compute an index associated with particular physiological parameter based on at least three dimensions. Such an index can represent, for example, a parameter value, variations in the parameter value over time, and a frequency of changes in the parameter value. For instance, the parameter value can calculate a desaturation index. The desaturation index can be used, for example, to alert a clinician of several relatively minor desaturation events over time. The relatively minor desaturation events may not individually indicate a clinically significant event, but minor desaturation within a certain period of time may warrant additional attention from a clinician. In some embodiments, the desaturation index can represent a drop in $SpO_2$ from a baseline value over time and the number of times that the $SpO_2$ value drops below a threshold for a predetermined period of time. In some instances, the threshold and the predetermined period of time can be based on an alarm pattern.

Alternatively or additionally, at least one dimension of an index can be based on user input. For example an index can represent a perfusion index (PI) and a user defined change in the PI within a predetermined amount of time.

An alarm pattern can be selected by the alarm pattern selector 220. The alarm pattern selector 220 can be included, for example, as part of the processor 190 (FIG. 1). Patient characteristic data can be provided to the alarm pattern selector 220, for example, via an electronic file, manual input by a clinician or other user, from other data stored by the physiological monitor related to a patient (e.g., physiological data obtained from one or more sensors and/or parameters/indexes calculated by the parameter calculator 210), the like, or any combination thereof. The patient characteristic data may relate to the patient and/or conditions of the patient. Based on the patient characteristic data, the alarm pattern selector 220 can select a pattern for a particular patient. In this way, alarms can be generated for patients based on an alarm pattern chosen specifically for the patient. An alarm pattern may include a plurality of threshold values, a corresponding period of time for each of the plurality of threshold values, a baseline value, or any combination thereof. More details regarding illustrative theresholding models that can correspond to alarm patterns will be provided later with reference to FIGS. 3A through 4D.

Alarm patterns may correspond to specific physiological parameter(s). Accordingly, the alarm pattern selector 220 can also select a pattern based on physiological data provided to the parameter calculator, the one or more physiological parameters calculated by the parameter calculator 210, data provided by another source, or any combination thereof. For example, when a sensor provides the parameter calculator 210 physiological data related to $SpO_2$, the alarm pattern selector 220 can select an alarm pattern corresponding to $SpO_2$. As another example, when the parameter calculator 210 provides the alarm generator 230 with a calculated $SpO_2$ value, the alarm pattern selector 220 can select a pattern based on the patient characteristic data and the $SpO_2$ value. In this way, the alarm pattern selector 230 can provide the alarm generator 230 with an alarm pattern corresponding to the physiological parameter(s) provided by the parameter calculator 210.

In some instances, the alarm pattern can be selected based on patient characteristic data. Some examples of patient characteristic data can include, but are not limited to, age, weight, gender, specific patient conditions (e.g., apnea, whether the patient has a pacemaker, etc.), patient habits (e.g., smoking and/or drug use), body mass index (BMI), family medical history data, historical or baseline physiological parameter values, and the like. For instance, the alarm pattern selector 220 may select an alarm pattern based on the patient's age included in an electronic file and/or entered at the direction of a user of the physiological monitor. In an illustrative example, neonatal patients can experience narrow oxygen desaturations and adult patients can experience broad oxygen desaturations. Advantageously, in certain embodiments, the alarm pattern selector 220 selects an $SpO_2$ alarm pattern associated with one set of threshold values for the neonatal patient and an alarm pattern with another set of threshold values for the adult. Similarly, healthier patients, as indicated by BMI, non-smoking habits, quantity/frequency of exercise, and/or other factors, may be assigned a different alarm pattern by the alarm pattern selector 220 than less healthy patients. An athlete having a heart rate of 40 BPM, for instance, might be less cause for concern than a smoker having the same heart rate. Thus, a different alarm pattern could be selected for the athlete than a smoker.

The alarm pattern selector 220 can also select an alarm pattern based on conditions of a patient provided as part of or derived from the patient characteristic data. Some patient condition data can include, but are not limited to, a period of time since a clinically significant event and/or patient treatment, a period of time that a patient has been asleep, temperature of the patient's surroundings, any other indicator that can affect physiological parameters values of the patient, or any combination thereof. For example, oxygen desaturations can be more clinically significant while a patient is sleeping compared to when the patient is awake and has more stable $SpO_2$ values. To account for this, the alarm pattern selector 220 can select a $SpO_2$ alarm pattern based on indicator(s) that the patient is likely to be asleep, for example, based on time of day, slower respiratory rate, lowered heart rate, combinations of the same, nurse or video monitoring indicating that the patient is asleep, and the like.

In some instances, the alarm pattern selector 220 may identify two or more different alarm patterns that can be used for a particular patient. In such instances, the alarm pattern selector 220 can select one of these alarm pattern based on which alarm pattern is determined to be more relevant to or important for the particular patient and/or has the closest match with the patient. For example, each alarm pattern can be associated with an importance value, and the alarm pattern selector 220 can select the alarm pattern with the highest importance value for a patient when two or more patterns match a particular patient. For instance, if the patient is a cardiac patient, the alarm pattern selector 220 may select a cardiac-related alarm pattern over a feasible non-cardiac alarm pattern. As another example, each alarm pattern can have a match score that indicates how closely the alarm pattern matches the patient, and the alarm pattern selector 220 can select the alarm pattern with the highest match score for the patient. In some implementations, the alarm pattern selector 220 can select an alarm pattern based on the importance score and the match score.

Alternatively or additionally, the alarm pattern selector 220 can modify and/or customize an alarm pattern for a particular patient. More details regarding modifying and/or customizing an alarm pattern will be provided later, for example, with reference to FIG. 6.

The alarm generator 230 can generate an alarm based on the physiological parameter data obtained from the parameter calculator 210 and the alarm pattern obtained from the alarm pattern provided by the alarm pattern generator 220. The alarm generator 230 can be included, for example, as part of the processor 190 (FIG. 1). The alarm generator 230 can compare physiological parameter(s) to the alarm pattern over time to determine whether to generate an alarm. For example, the alarm generator 230 can generate an alarm when a physiological parameter satisfies one of the plurality of threshold values of the alarm pattern for the corresponding period of time associated with the one threshold value.

If a threshold of an alarm pattern is satisfied, the alarm generator 230 can cause an audio and/or visual alarm to be provided to a clinician. The alarm can be presented to the clinician, for example, via a monitor and/or a speaker in communication with the alarm generator 230. The monitor and/or speaker can be part of the physiological monitoring system 200 that includes the alarm generator 230 or separate from the physiological monitoring system 200. In some instances, the alarm generator 230 can cause transmission of the alarm to a user device via a network.

Referring now to FIGS. 3A through 4D, several alarm patterns or thresholding models are shown. Each alarm pattern can include a plurality of threshold values and one or more corresponding periods of time associated with each of the plurality of threshold values. Each threshold value can be set based on historical values. The historical values can be associated with all people, any demographic, a specific patient, or any combination thereof. In some embodiments, the alarm pattern can also include a baseline value. The baseline value may change over time. Each threshold value can be set to correspond to a particular parameter value and/or to a percentage of a baseline value. In FIGS. 3A through 4D, the example alarm patterns shown are not drawn to scale and instead serve to show example features of alarm patterns. Any combination of features described in connection with any one of these example alarm patterns can be applied to any other alarm pattern in certain embodiments.

FIG. 3A illustrates an embodiment of an alarm pattern 310 for $SpO_2$. Any point on the alarm pattern curve, illustrated by a solid line 311, can correspond to a threshold value. Example threshold values are shown, including 90% saturation, 85%, and so forth down to 70% saturation. The alarm pattern 310 can achieve a desired granularity by including any suitable number of thresholds and corresponding periods of time.

A period of time for each threshold is depicted as a horizontal line 312 between the solid lines 311 and corresponding to the same parameter value. The lower the saturation threshold value, the shorter the period of time is that may trigger an alarm. For example, the period of time for a 90% saturation threshold might be 30 seconds, while a threshold of 85% can have a corresponding period of time of 15 seconds in some implementations, and a threshold at 70% saturation can be 5 seconds. Thus, if a patient's saturation is below 85% for 15 seconds in this example, an alarm can be triggered. An example patient saturation curve 314 is shown. The saturation curve 314 does not drop below 85% for the corresponding full period of time due to a portion 316 of the curve 314 exceeding 85% saturation. Thus, an alarm is not generated based on the 85% threshold in this example. Accordingly, nuisance alarms that might otherwise occur as a result of a noisy signal or the like can be avoided or reduced.

The alarm pattern 310 illustrated in FIG. 3A can represent an alarm pattern in which a lower parameter value (e.g., $SpO_2$ value) becomes progressively more life-threatening. This can be a default alarm pattern generated from historical data. A default alarm pattern can be useful when a parameter value is similar for a segment of the population. The default alarm pattern can be modified to reflect a patient's baseline parameter value. For example, the threshold values can be based on percentages of the patient's baseline parameter value rather than the absolute parameter value. In another embodiment, the default alarm pattern can be modified based on any of the other patient characteristics described above. For example, if the patient is sleeping, the time periods for each saturation threshold can be shortened, or a different alarm pattern 310 may be selected for the patient.

Any of the principles of comparing a parameter value to an alarm pattern over time can also be used for a multi-parameter index by comparing the index to an alarm pattern over time. The index may represent any suitable combination of two or more parameters, such as any of the indices described above. An alarm pattern similar to the pattern 310 of FIG. 3A can be used for an index. However, FIG. 3B illustrates a different type of alarm pattern 320 that can also be used with a multi-parameter index.

The alarm pattern 320, illustrated by a solid line, can represent an alarm pattern similar to the alarm pattern illustrated in FIG. 3A. However, the alarm pattern curve of FIG. 3B can group the index value (or a percentage of a baseline index value) into a stepwise curve that includes buckets. A bucket can be represented by a range and a corresponding period of time. The range can be defined by the difference between two threshold values. In the alarm pattern, the period of time can be associated with both threshold values that define the range. Thus, a period of time can be associated with more than one threshold value, since the period of time can correspond to both threshold values defining the range. Similarly, more than one period of time can be associated with a threshold value, since the threshold value can be used to define ranges for two buckets. In the alarm pattern curve of FIG. 3B, a first bucket can have a range of 2-3 (index value) and a first period of time, a second bucket can have a range of 3-4 and a shorter period of time, and a third bucket can have a range of 4-5 and an even shorter period of time.

In one embodiment, when the index value stays within a range for the corresponding period of time, an alarm can be generated. Alternatively, when an index value stays below a threshold 322 for a period of time defined by the width of the alarm pattern 320, an alarm can be generated. For example, a curve 324 depicting a changing index value over time is below the "3" threshold (322) for the time period defined by the width of the alarm pattern 320, and therefore an alarm may be generated.

FIGS. 4A through 4D graphically illustrate additional examples of alarm patterns 410-440 for a physiological parameter. The physiological parameter can be, for example, any of the physiological parameters described herein. Although described in the context of physiological parameters for ease of illustration, the alarm patterns 410-440 can also be applied to an index as described above.

The alarm patterns 410-440 (or other alarm patterns) can correspond to a number of different parameters, patient conditions, patient characteristics, environments, the like, or any combination thereof. Threshold value(s) and/or corresponding period(s) of time of an alarm pattern for such alarm patterns can be tailored for any of these considerations. For example, an alarm pattern can be specifically tailored for a cardiac patient, an obese cardiac patient, a female cardiac patient, a neonatal cardiac patient, a patient with a pacemaker, etc. Tailoring an alarm pattern for a specific patient can reduce the number and/or frequency of nuisance alarms that are generated.

Figure 4B:
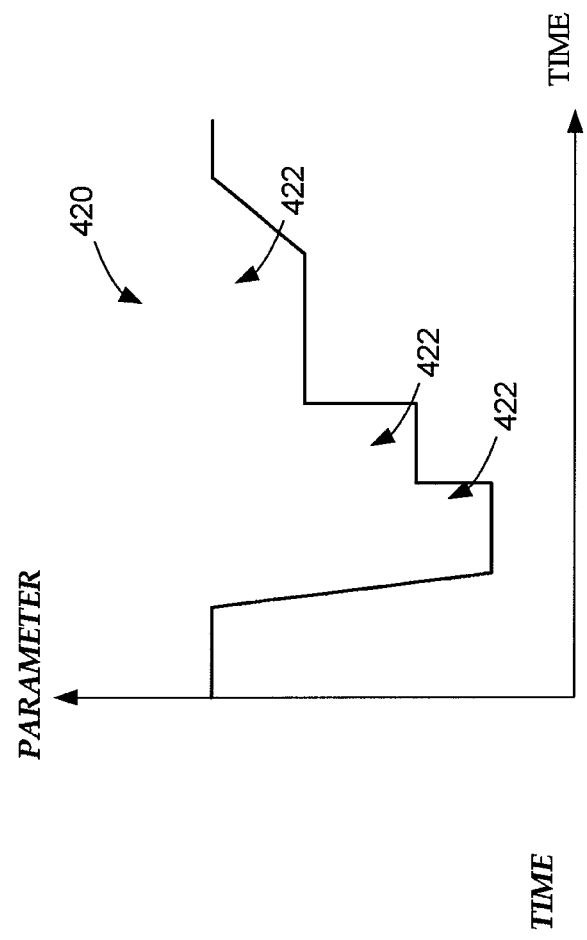
FIGS. 4A through 4D graphically illustrate various embodiments of alarm patterns for a physiological parameter.
Figure 4A:
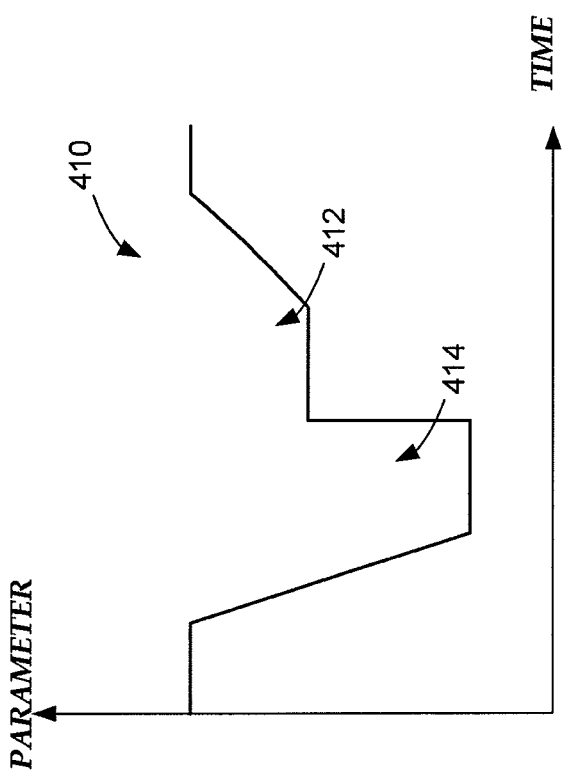

FIG. 4A illustrates a stepwise alarm pattern 410 with two steps. The alarm pattern 410 has a broad period of time 412 for a first range of parameter values and a narrow period of time 414 for a second range of parameter values. This disparity in alarm periods 412, 414 can separate out two different conditions and/or two different severities of different parameter value ranges.

In one embodiment, the alarm pattern 410 can be used for a cardiac patient who has had heart problems. Some cardiac patients are more sensitive to deeper desaturations than other patients. Thus, having a narrower period of time 414 for deep desaturations (e.g., 80-85% $SpO_2$ or less) can trigger an alarm sooner than might otherwise occur with another alarm pattern. As illustrated in FIG. 4B, some alarm patterns (420) can include stepwise patterns with more than two steps 422. Such a pattern 420 can be used for certain cardiac patients instead of the pattern 410 to provide more granularity in monitoring deep desaturations.

Figure 4D:
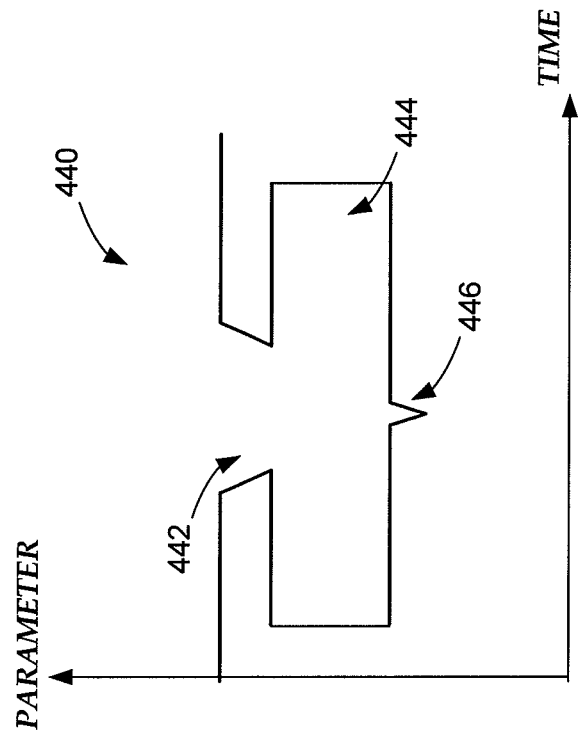
Figure 4C:
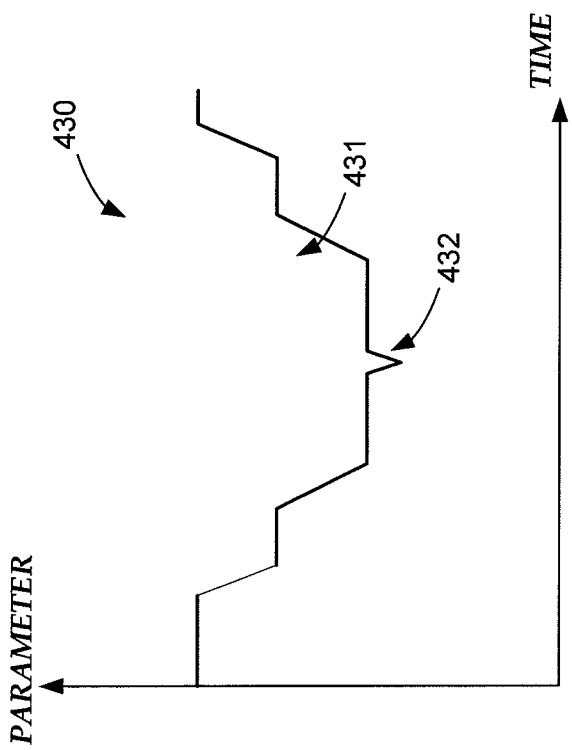

Alarm patterns can be used to generate an alarm when potentially unsafe parameter levels occur for a short period of time, for example, as illustrated in FIG. 4C. The alarm pattern 430 shown can allow parameter levels to be within a range 431 above a potentially unsafe parameter level for a period of time that is notably longer than the short period of time 432 (e.g., about 2, about 5, about 10, or about 20 times longer or more). In this way, the alarm pattern can generate alarms for brief but deep deviations in a parameter value that indicate a potentially serious condition and still allow the parameter value to be slightly above the potentially unsafe value for a longer period of time.

In an illustrative example, the parameter of FIG. 4C can be $SpO_2$ and the alarm pattern can be for a patient that is sleeping. When a patient is awake, $SpO_2$ values may be more stable than while asleep. Thus, it may be more important to alarm for brief but deep desaturations for a sleeping patient than for a patient that is awake.

Alarm patterns can also be discontinuous and/or include ranges of associated with parameter values for which alarms may not be generated, as illustrated in FIG. 4D. For example, some ranges 444 of parameter values may be acceptable, yet higher and/or lower ranges 442, 446 can indicate clinically significant events. While no alarm may be generated for a desired parameter range 444, alarms can be generated for parameter values above and below the desired parameter range 444. The alarm pattern 440 shown in FIG. 4D is also asymmetric on each side of the desired range 444, although this asymmetry is optional. The alarms for this type of alarm pattern 440 can be generated so that a clinician can help bring the parameter value back into the desired range 444. In this way, the alarm pattern 440 can be used to help keep a parameter within the desired range 444.

In an illustrative example, the parameter of FIG. 4D can be heart rate and the alarm pattern 440 can be used for a patient with an implanted pacemaker. When the heart rate is within a pacesetting range (444), the pacemaker may be operating properly because the patient's heart rate is close to a paced beat. Accordingly, no alarm may be generated if the patient's heat rate is within the pacesetting range 444. However, when the patient's heart rate goes outside of the pacesetting range, this can indicate a clinically significant event. For example, when heat rate goes above the pacesetting range 444 (e.g., in the range 442), the patient's heart is beating faster than the pacemaker. Thus, an alarm can be generated if heart rate is above the pacesetting range 444 for a period of time. As another example, when the patient's heart rate falls below the pacesetting range 444 (e.g., to 446), this can indicate that the pacemaker is not firing or otherwise not working. If this happens for even a short period of time, an alarm can be generated so that a clinician can check the pacemaker. Many other variations are possible.

Figure 5:
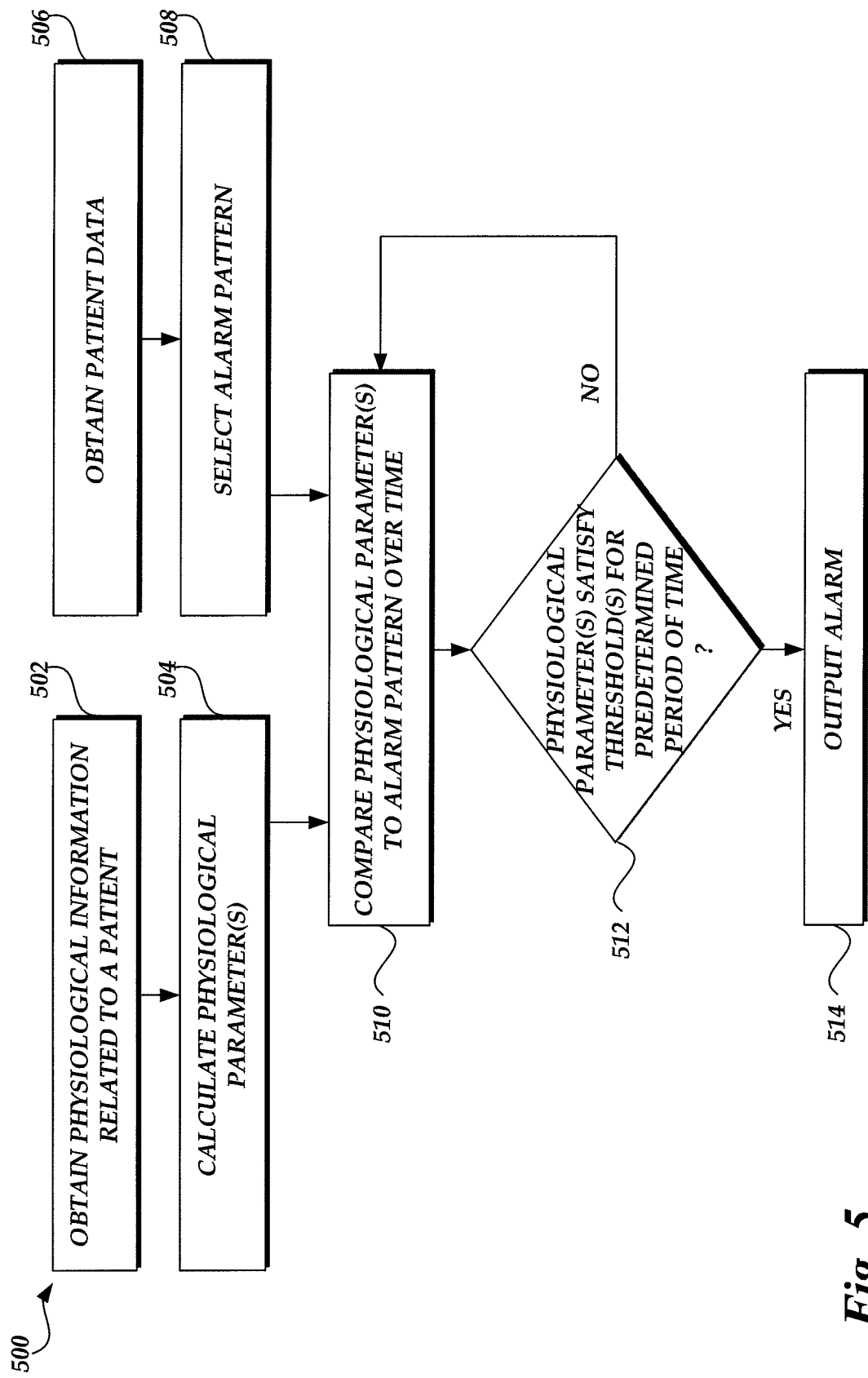
FIG. 5 is a flow diagram of an illustrative method of outputting an alarm in accordance with an embodiment.
Figure 6:
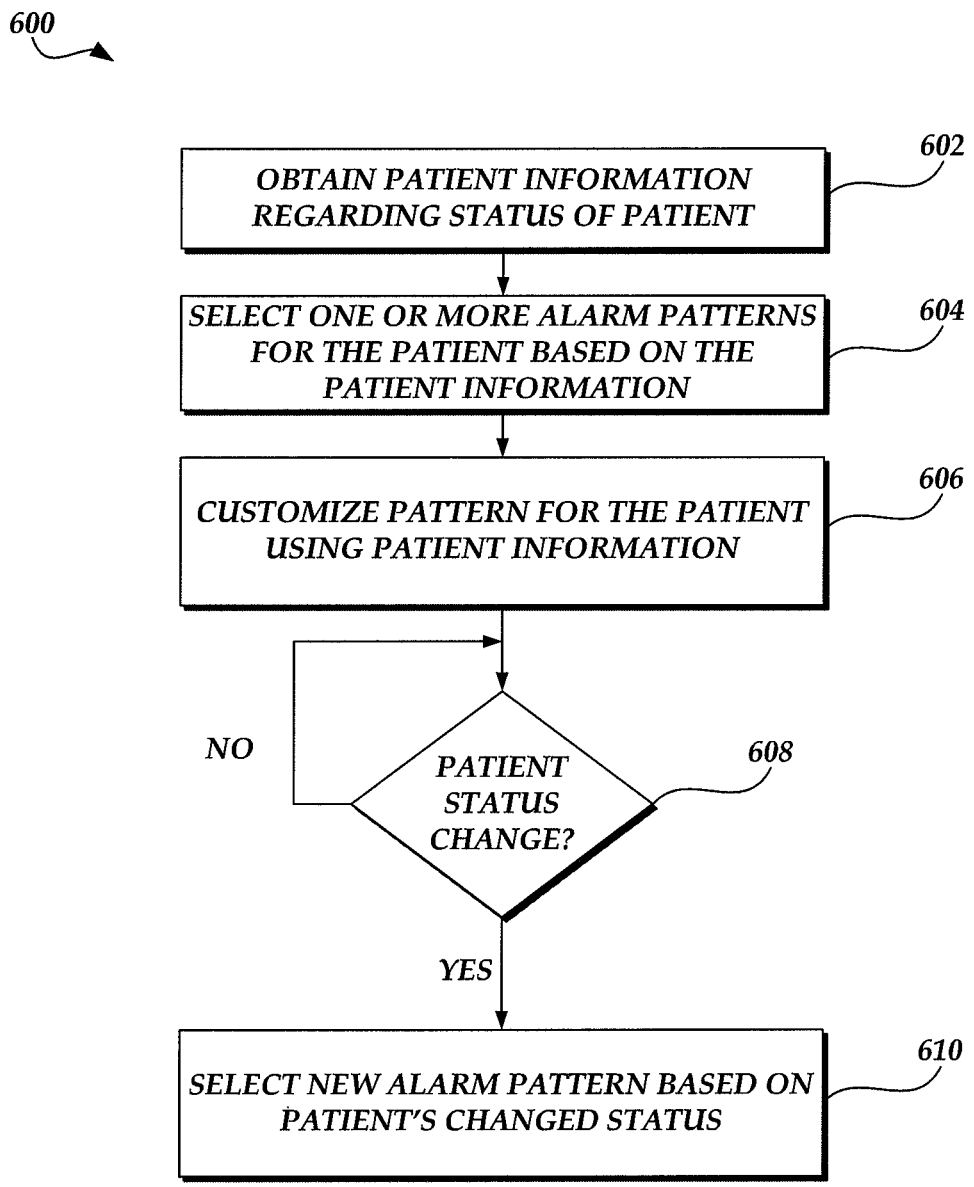
FIG. 6 is a flow diagram of an illustrative method selecting an alarm pattern in accordance with an embodiment.

FIGS. 5 and 6 illustrate example methods for selecting an alarm pattern. In addition, the method of FIG. 5 includes generating an alarm based on the selected alarm pattern. These methods can be implemented, for example, with the physiological monitor 100 or the physiological monitoring system 200, any suitable patient monitor, or any combination thereof.

Referring to FIG. 5, a flow diagram of an illustrative method 500 of outputting an alarm will be described. The method 500 can include obtaining one or more physiological parameters. Physiological patient information can be obtained at block 502. Based on the physiological patient information, one or more physiological parameters can be calculated at block 504. The method 500 can also include selecting an alarm pattern. Patient information can be obtained at block 506.

At block 508, an alarm pattern can be selected based on the patient data. The alarm pattern can also be selected based on the physiological parameter(s) computed at block 504 and/or physiological data obtained at block 502, in some implementations. Selecting the alarm pattern can include, for example, any combination of features described with reference to the alarm pattern selector 220 (FIG. 2). Further, selecting the alarm pattern can include any of the features that will be described later with reference to the method 800 (FIG. 8). The alarm pattern can be selected dynamically, at predetermined periods of time (e.g., every 10 minutes, hour, day, etc.), in response to a triggering event (e.g., access to new data, changes in patient conditions and/or physiological parameter values, powering on a patient monitor, etc.), at the direction of a clinician or other user, or any combination thereof.

The selected alarm pattern can be compared over time to the calculated physiological parameter at block 510. The comparison can include determining if the physiological parameter satisfies at least one of a plurality of thresholds of the alarm pattern for a predetermined period of time. Alternatively or additionally, the comparison can include determining if the physiological parameter is within a range defined by two thresholds of a plurality of thresholds of the alarm pattern for a predetermined period of time. In response to the physiological parameter satisfying a predetermined threshold of the alarm pattern for a predetermined period of time at decision block 512, an alarm can be output at block 514. Conversely, in response to the physiological parameter not satisfying the predetermined threshold of the alarm pattern for a predetermined period of time at decision block 512, the method 500 can return to block 510 and continue to compare the physiological parameter to the alarm pattern.

Referring to FIG. 6, a flow diagram of an example method 600 of selecting an alarm pattern in accordance with an embodiment will be described. The method 600 can be performed, for example, in connection with blocks 506 and 508 of the method 500. Patient information regarding a status of a patient can be obtained at block 602. The patient information can include, for example, any of the patient information described herein related to patient characteristics, status of the patient and/or an environment of the patient. The patient information can be obtained by receiving user input, by receiving data from a sensor, from an electronic file, or using any suitable method.

At block 604, one or more alarm patterns can be selected based on the patient information. In one embodiment, an alarm pattern can be selected using the alarm pattern selector 220 (FIG. 2). The selected pattern can include, for example, any of the alarm patterns described earlier in reference to FIGS. 3A through 4D.

The selected alarm pattern can be customized using patient information at block 606. For instance, one or more threshold values, one or more periods of time corresponding to threshold values, one or more baseline values, or any combination thereof can be adjusted based on patient information as described above. Alternatively or additionally, an alarm pattern can be customized by combining two or more alarm patterns corresponding to patient data for a particular patient. For example, if two of the alarm patterns illustrated in FIGS. 3A through 4D correspond to a patient, features of the two patterns can be used to generate a new pattern.

At block 608, the patient's status can be monitored. A change in status may be determined, for example, based on changes in one or more parameter values. For example, a lower respiration rate and/or progressively decreasing oxygen desaturations can indicate that a patient is asleep. The longer a patient is asleep, lower levels of oxygen desaturation can be expected. The change in status can also be determined by a change in any of the patient characteristic data associated with the patient.

In response to there being no change in status, the patient's status can be continued to be monitored for changes. In contrast, when a change in the patient's status is detected, a new alarm pattern can be selected at block 610. The new alarm pattern can be selected based on the patient's changed status. For example, if the change in status was detected based on a change in a physiological parameter value, the new alarm pattern can be selected based on the change in the physiological parameter value. For instance, a worse parameter value can decrease a time associated with a threshold of an alarm pattern and a better parameter value can increase a time associated with a threshold of an alarm pattern. Thresholds can be adjusted similarly. In a specific example, to account for a patient being asleep longer, one or more thresholds and/or corresponding periods of time can be adjusted so that greater oxygen desaturations are more likely to generate an alarm when the patient has been asleep longer. The new alarm pattern can be selected based on any combination of the principles and advantages used to select the original alarm pattern.

Figure 7:
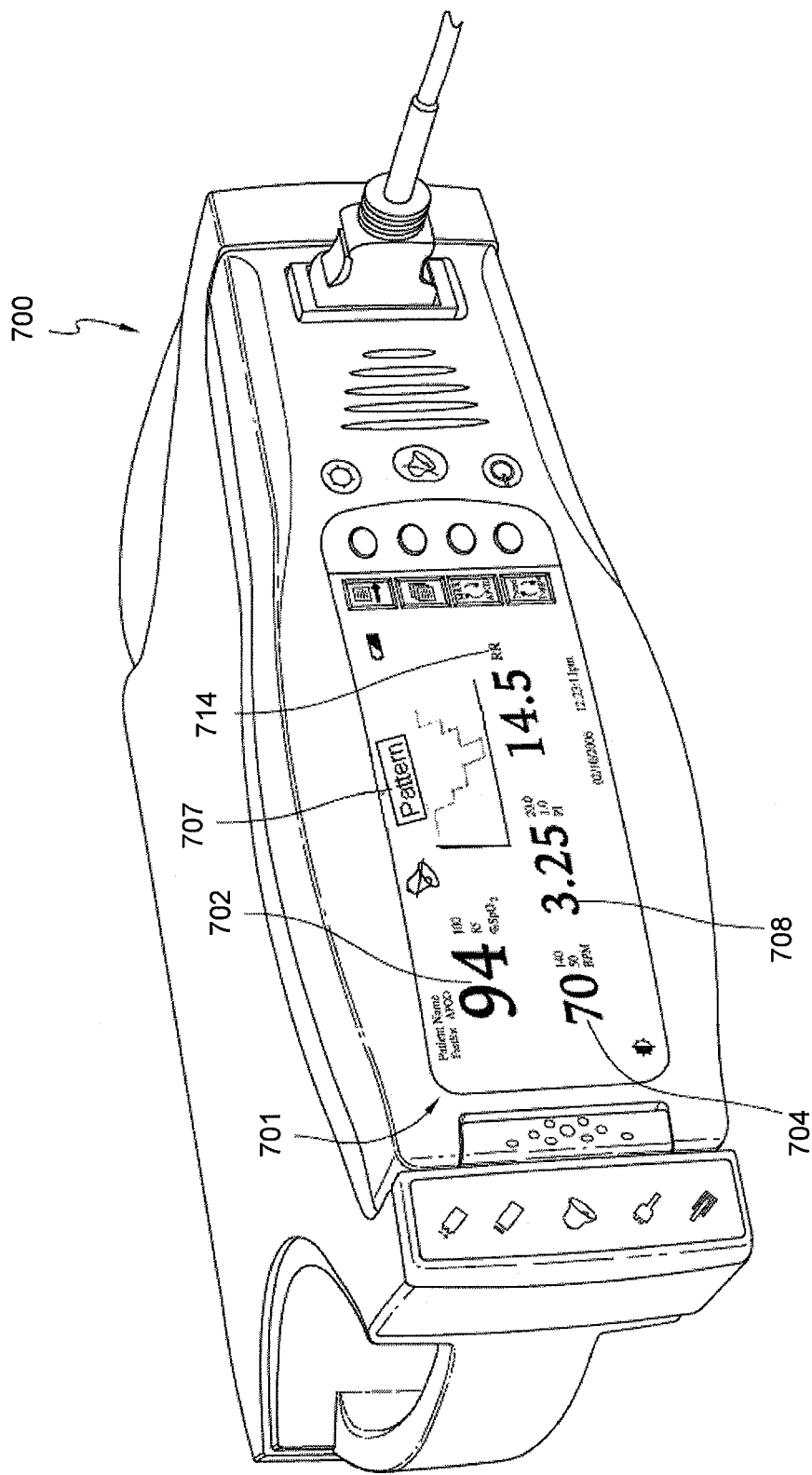
FIG. 7 illustrates an embodiment of display having an interface for selecting an alarm pattern.

FIG. 7 illustrates an example physiological monitor 700 that can implement any combination of the features described herein. The physiological monitor 700 can include an interface for selecting an alarm pattern, for example, any of the alarm patterns described herein. An embodiment of the physiological monitor 700 includes a display 701 showing data for multiple physiological parameters. For example, the display 701 can include a CRT and/or an LCD display including circuitry similar to that available on physiological monitors commercially available from Masimo Corporation of Irvine, Calif. sold under the name Radical™, and disclosed in, for example, U.S. Pat. Nos. 7,221,971; 7,215,986; 7,215,984 and 6,850,787, the disclosures of which are hereby incorporated by reference in their entirety. However, many other display components can be used that are capable of displaying $SpO_2$, respiratory rate and other physiological parameter data along with the ability to display graphical data such as alarm patterns, plethysmographs, respiratory waveforms, trend graphs or traces, and the like.

The display 701 can display one or more alarm patterns 707. The physiological monitor 700 can receive commands from a user related to selecting, customizing, modifying, and/or verifying an alarm pattern. For example, an interface can include a touch screen and/or one or more selection elements (e.g., buttons or knobs) to enable a user to provide commands to the physiological monitor 700.

In some embodiments, the interface of the physiological monitor 700 can enable a clinician (e.g., an anesthesiologist) or another user to select an alarm pattern 707. For example, the clinician can evaluate a patient's chart and select an alarm pattern based on information in the chart, other patient information, patient conditions, or observation by the clinician, or any combination thereof. The interface can enable the clinician to browse a plurality of alarm patterns (e.g., corresponding to any combination of features of the thresholding models described in reference to FIGS. 3A through 4D) and select a desired alarm pattern. In some embodiments, the interface can also allow a clinician to set one or more thresholds, corresponding periods of time and/or baselines for an alarm pattern, modify a shape of an alarm pattern, create a new alarm pattern, or any combination thereof.

Alternatively or additionally, the physiological monitor 700 can select an alarm pattern 707 for a patient, for example, using any combination of features described in reference to the method 600 (FIG. 6). The alarm pattern 707 can be displayed in response to selecting the alarm pattern and/or at the direction of a user. A clinician (e.g., an anesthesiologist) can evaluate the alarm pattern 707 to verify that the alarm pattern 707 selected by the patient monitor 700 is appropriate for a particular patient. Verification by a clinician can provide an additional check to make sure that the selected alarm pattern is appropriate for a particular patient. In addition, verification by a clinician can account for additional patient information that may not be reflected in data available to the patient monitor 700. In some embodiments, the interface can enable the clinician to send a command verifying that the selected pattern is appropriate for use with a particular patient. The interface can also enable the clinician or another user to modify the pattern selected by the physiological monitor 700 and/or select a different alarm pattern.

The display 701 can also display one or more physiological parameters and/or one or more indexes, which can combine two or more physiological parameters. These values can be obtained from, for example, the parameter calculator 210 (FIG. 2). One or more of the parameters and/or indexes can be compared to an alarm pattern, for example, using any combination of features described in reference to the method 700 (FIG. 7).

The depicted embodiment of the display 701 shows measured values of $SpO_2$ 702, a pulse rate 704 in beats per minute (BPM), a respiratory rate (RR) 714 in breaths per minute, and a perfusion index (PI) 708. Many other physiological parameters can be measured and displayed by the multiparameter physiological monitor 700, such as blood pressure, ECG readings, $EtCO_2$ values, bioimpedance values, and the like. In some embodiments, multiple respiratory rates or other parameter values, corresponding to multiple input sensors and/or monitors, can be displayed.

TERMINOLOGY

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently, e.g., through multi-threaded processing, interrupt processing, or multiple processors or processor cores, rather than sequentially.

The various illustrative logical blocks, modules, circuits, and algorithm operations described in connection with the embodiments disclosed herein can be implemented as electronic hardware, computer software, or combinations of both. To clearly illustrate this interchangeability of hardware and software, various illustrative components, blocks, modules, circuits, and operations have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others. The scope of certain inventions disclosed herein is indicated by the appended claims rather than by the foregoing description. All changes which come within the meaning and range of equivalency of the claims are to be embraced within their scope.

What is claimed is:

1. A method for reducing nuisance alarms, the method comprising:

receiving physiological information associated with a patient;

calculating a plurality of values for a physiological parameter over time associated with the patient based at least in part on the received physiological information;

selecting, under control of one or more processors, an alarm pattern from a first alarm pattern or a second alarm pattern based at least in part on a characteristic of the patient, the alarm pattern including:

said first alarm pattern including a first threshold having a corresponding first threshold time that indicates a period of time that values of said physiological parameter have crossed the first threshold before generating a first alarm; and said second alarm pattern including a second threshold having a corresponding second threshold time that indicates a period of time that values of said physiological parameters have crossed the second threshold before generating a second alarm; wherein the second threshold time is smaller than the first threshold time and wherein the second alarm pattern corresponds to a time of day when the patient is asleep;

determining a first length of time that the calculated plurality of values for the physiological parameter have crossed the first threshold;

determining a second length of time that the calculated plurality of values for the physiological parameter have crossed the second threshold;

comparing the first length of time with the first threshold time;

comparing the second length of time with the second threshold time;

generating a first alarm based on said comparing the first length of time with the first threshold time; and generating a second alarm based on said comparing the second length of time with the second threshold time.

2. The method of claim 1, wherein said selecting is further based on the received physiological information.

3. The method of claim 1, wherein the physiological parameter includes one of the following: oxygen saturation, respiratory rate, and heart rate.

4. The method of claim 1, wherein the alarm pattern further includes a baseline.

5. The method of claim 1, wherein the physiological information is received from one or more sensors.

6. A method for reducing nuisance alarms, the method comprising:

receiving a physiological parameter associated with a patient;

storing a first alarm pattern corresponding to a first time of a day, the first alarm pattern including a plurality of first thresholds each having corresponding first periods of time;

storing a second alarm pattern corresponding to a second time of a day, the second alarm pattern including a plurality of second thresholds each having corresponding second periods of time, wherein said second time of a day corresponds to when the patient is asleep;

determining, under control of one or more processors, a time of day;

selecting an alarm pattern from the first or the second alarm pattern based at least on the determination of the time of day; and determining whether to generate an alarm based at least in part on a comparison over time of the physiological parameter to a value computed using the selected alarm pattern.

7. The method of claim 6, further comprising selecting a new alarm pattern based at least in part on a change in status of the patient.

8. The method of claim 6, further comprising setting at least one threshold of the plurality of the first or the second thresholds based at least in part on a characteristic of the patient.

9. The method of claim 6, further comprising setting at least one period of time corresponding to at least one of the plurality of the first or the second thresholds based at least in part on a characteristic of the patient.

10. The method of claim 6, wherein said selecting is performed in response to a user selecting the alarm pattern.

11. The method of claim 6, further comprising generating the alarm.

12. An system for reducing nuisance alarms, the system comprising:

one or more processors configured to:

receive physiological parameter data associated with a patient;

select an alarm pattern from a first alarm pattern or a second alarm pattern based at least in part on an indicator of an attribute of the patient, said first alarm pattern including a first threshold having a corresponding first threshold time that indicates a period of time that the physiological parameter data has crossed the first threshold before generating a first alarm; and said second alarm pattern including a second threshold having a corresponding second threshold time that indicates a period of time that the physiological parameter data has crossed the second threshold before generating a second alarm; wherein the second threshold time is smaller than the first threshold time and wherein the second alarm pattern corresponds to a time of day when the patient is asleep;

determine a first length of time that the physiological parameter data for the physiological parameter has crossed the first threshold;

determine a second length of time that the calculated plurality of values for the physiological parameter have crossed the second threshold;

compare the first length of time with the first threshold time;

compare the second length of time with the second threshold time;

generate a first alarm based on said comparing the first length of time with the first threshold time; and generate a second alarm based on said comparing the second length of time with the second threshold time.

13. The system of claim 12, wherein the one or more processors are further configured to generate an alarm when the physiological parameter data is within a range for a predetermined period of time associated with the range.

14. The system of claim 12, wherein the value associated with the physiological parameter is a multi-parameter index.

15. The system of claim 14, wherein the one or more processors are further configured to compute the multi-parameter index based on the physiological parameter data.

16. The system of claim 12, wherein the indicator of the attribute of the patient is based on one or more of the following: age, gender, height, and weight.

17. The system of claim 12, wherein the one or more processors are further configured to enable a user to select the alarm pattern.

18. The system of claim 12, wherein the one or more processors are further configured to enable a user to adjust the alarm pattern.

19. The method of claim 1, further comprising determining a time of day and updating the selected alarm pattern based on the determined time of day.

20. The system of claim 12, wherein the one or more processors are further configured to determine a time of day and update the selected alarm pattern based on the determined time of day.

* * * * *